United States Patent
Dolan et al.

(10) Patent No.: US 6,920,677 B2
(45) Date of Patent: Jul. 26, 2005

(54) METHOD FOR MANUFACTURING AN ENDOVASCULAR SUPPORT DEVICE

(75) Inventors: Mark J. Dolan, Santa Rosa, CA (US); Justin Goshgarian, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/377,489

(22) Filed: Feb. 27, 2003

(65) Prior Publication Data

US 2004/0168298 A1 Sep. 2, 2004

(51) Int. Cl.[7] ............................................... B23P 13/04
(52) U.S. Cl. ................. 29/557; 623/901; 623/1.11; 83/178; 83/54
(58) Field of Search .................. 623/1.11, 1.2, 623/901, 1.12; 29/557, 2.1; 83/54, 178; 219/121.71

(56) References Cited

U.S. PATENT DOCUMENTS

| | | | |
|---|---|---|---|
| 3,965,620 A | | 6/1976 | Dreher |
| 5,780,807 A | * | 7/1998 | Saunders ............. 219/121.71 |
| 5,836,965 A | | 11/1998 | Jendersee et al. |
| 5,885,258 A | * | 3/1999 | Sachdeva et al. ......... 604/530 |
| 5,925,061 A | | 7/1999 | Ogi et al. |
| 5,984,973 A | * | 11/1999 | Girard et al. .................... 1/1 |
| 6,206,755 B1 | | 3/2001 | Samsel |
| 6,379,379 B1 | * | 4/2002 | Wang ......................... 623/1.15 |
| 6,425,855 B2 | * | 7/2002 | Tomonto ...................... 600/36 |
| 2002/0055769 A1 | | 5/2002 | Wang |
| 2003/0187498 A1 | * | 10/2003 | Bishop ....................... 623/1.16 |

FOREIGN PATENT DOCUMENTS

| | | |
|---|---|---|
| EP | 0 951 877 A2 | 10/1999 |
| EP | 0 951 877 A3 | 1/2000 |
| EP | 1 288 637 A1 | 12/2002 |
| WO | WO-03/082150 A1 | 10/2003 |
| WO | PCT/US03/41649 | 5/2004 |

* cited by examiner

*Primary Examiner*—David P. Bryant
*Assistant Examiner*—Stephen Kenny

(57) ABSTRACT

A method for manufacturing an endovascular support device comprises positioning a generally tubular member made of an implantable metal and having a generally cylindrical wall in a working relationship with a laser beam. A desired pattern is cut in the generally cylindrical wall in order to produce a stent having a plurality of openings and a plurality of edges. The stent is tumbled in a medium to round its edges and, in turn, to produce more rounded cross-sections of stent elements.

15 Claims, 3 Drawing Sheets

METHOD FOR MANUFACTURING AN ENDOVASCULAR SUPPORT DEVICE

TECHNICAL FIELD

This invention relates generally to endovascular support devices, and more particularly, to an improved method for manufacturing a stent having a smooth profile and edgeless geometry.

BACKGROUND OF THE INVENTION

Cardiovascular disease is a leading cause of death, and as a result, the medical community has devised various methods and devices for the treatment of coronary heart disease including those associated with the complications resulting from atherosclerosis or other forms of coronary arterial closing or narrowing. One such treatment utilized in cases involving atherosclerosis and/or other forms of coronary narrowing is referred to as percutaneous transluminal coronary angioplasty, sometimes simply referred to as angioplasty or PTCA. The objective of this technique is to radially enlarge the lumen of the impacted artery. This is accomplished by first positioning an expandable balloon in a target lesion (i.e., the narrowed lumen of the coronary artery). Inflation of the balloon causes (1) soft or fatty plaque deposits to be flattened by the balloon and (2) hardened deposits to crack and split thereby enlarging the lumen. In addition, the artery wall itself is stretched by the inflated balloon.

In a typical percutaneous transluminal coronary angioplasty (PTCA) procedure, a hollow guiding catheter is introduced into the cardiovascular system of a patient via a relatively large vessel such as the femoral artery in the groin area or the brachial artery in the arm. After access to the patient's cardiovascular system has been achieved, a short hollow sheath is inserted to maintain the passageway during the procedure. After the guiding catheter reaches the ostium of the coronary artery to be treated by angioplasty, a flexible guide wire and a dilatation catheter having a balloon on the distal end thereof are introduced into the guide catheter with the guide wire sliding through the dilatation catheter. The guide wire is advanced through a target lesion in the vasculature. A balloon or dilatation catheter (made of, for example, polyethylene, polyethylene terathalate, PEBAX (polyamide block copolymers and polyester block copolymers), polyvinyl chloride, polyolefin, nylon, or other suitable substance) is then slidably advanced over the previously advanced guide wire by sliding it along the guide wire until the dilatation balloon is properly positioned across the target lesion. Radiopaque markers in the balloon portion of the dilatation catheter assist in the positioning of the balloon across the lesion. After proper positioning, the balloon is inflated, generally with a contrast material to permit fluoroscopic viewing during the treatment, so as to enlarge the lumen of the artery. Treatment may require that the balloon be alternately inflated and deflated until satisfactory enlargement has been achieved. The balloon is then deflated to a small profile so that the dilatation catheter may be withdrawn from the patient's vasculature and blood flow resumed through the dilated artery. Unfortunately, after angioplasty procedures of this type, there may occur a restenosis of the artery; i.e. a renarrowing of the treated coronary artery that significantly diminishes any positive results of the angioplasty procedure. In the past, restenosis frequently necessitated repeat PTCA or even more drastic open-heart surgery.

To prevent restenosis and strengthen the target area, various devices have been proposed for mechanically keeping the affected vessel open after completion of the angioplasty procedure. Such mechanical endoprosthetic devices, generally referred to as stents, are typically inserted into the vessel, positioned across the target lesion, and then expanded to keep the lumen clear. A stent is mounted in a compressed state around a deflated balloon, and the balloon/stent assembly maneuvered through a patient's vasculature to the site of a target lesion. After positioning, the balloon is inflated causing the stent to be expanded to a larger diameter for placement or implantation in the vasculature. The stent effectively overcomes the natural tendency of the vessel walls of some patients to close back down, thereby permitting an increased flow of blood through the vessel that would not be possible if the stent were not in place.

Stents are generally tubular shaped devices which function to hold open a segment of blood vessel or other anatomical lumen. To be effective, the stent should be relatively flexible along its length so as to facilitate delivery through torturous body lumens, and yet stiff and stable enough when radially expanded to maintain the blood vessel or artery open. Such stents may include a plurality of axial bends or crowns adjoined together by a plurality of struts so as to form a plurality of U-shaped members coupled together to form a serpentine pattern.

Stents may be formed using any of a number of different methods. One such method involves forming segments from rings, welding or otherwise forming the stent to a desired configuration, and compressing the stent to an unexpanded diameter. Another such method involves machining tubular or solid stock material into bands and then deforming the bands to a desired configuration. While such structures can be made many ways, one low cost method is to cut a thin-walled tubular member of a biocompatible material (e.g. stainless steel, titanium, tantalum, super-elastic nickel-titanium alloys, high-strength thermoplastic polymers, etc.) to remove portions of the tubing in a desired pattern, the remaining portions of the metallic tubing forming the stent. Since the diameter of the stent is very small, the tubing from which it is made must likewise have a small diameter. Typically, the stent has an outer diameter of approximately 0.045 inch in its unexpanded configuration and can be expanded to an outer diameter approximately 0.1 inch or more. The wall thickness of the stent may be approximately 0.003 inch.

One method of cutting the tubing to produce a desired pattern is shown and described in U.S. Pat. No. 5,780,807 issued Jul. 14, 1998, and entitled "Method and Apparatus for Direct Laser-Cutting of Metal Stents", the teaching of which are hereby incorporated by reference. This patent describes a method of producing a laser-cut stent wherein the tubing is cut into a desired pattern by means of a machine-controlled laser. The tubing is fixed in a rotatable collet fixture of a machine-controlled laser apparatus so as to position the tubing relative to the laser beam. The tubing is then rotated and moved longitudinally relative to the laser in accordance with a predefined set of machine-encoded instructions. In this manner, the laser selectively removes material from the tubing by ablation, thus cutting a desired pattern into the tube and forming the stent.

It should be appreciated that direct laser-cutting produces edges which are essentially perpendicular to the axis of the laser beam. Thus, the laser-cutting process produces stent cross-sections that are substantially square or rectangular. It should further be appreciated that to facilitate insertion of the stent through a patient's vasculature while at the same time minimizing risk to the patient, the expandable stents are preferably comprised of fine geometries and smooth edges. Thus, the edges of the rectangular cross-sections in the stent elements produced by direct laser-cuttings should-be rounded and/or smoothed.

One known technique for converting the generally square or rectangular cross-section of the stent elements into a more rounded, somewhat circular cross-section is electropolishing. For example, as described in above-referred-to patent, the stents may be electrochemically polished in an acidic aqueous solution comprised of, for example, sulfuric acid, carboxylic acids, phosphates, corrosion inhibitors, and a biodegradable surface-active agent. The bath temperature may be maintained at temperature of approximately 110° Fahrenheit to 135° Fahrenheit at an appropriate current density. Unfortunately, such electropolishing processes present certain problems. For example, such techniques may be cumbersome and messy. Furthermore, such processes are difficult to control resulting in, for example, stent-to-stent and in-stent variations in cross-section.

It should therefore be appreciated that it would be desirable to provide an accurate, reliable, and cost effective method for manufacturing low-profile, edgeless-geometry stents.

SUMMARY OF THE INVENTION

According to a first aspect of the invention, there is provided a method for manufacturing an endovascular support device, comprising positioning a generally tubular member made of an implantable metal and having a generally cylindrical wall in a working relationship with a laser beam. A desired pattern is then laser-cut in the generally cylindrical wall in order to produce a laser-cut stent having a plurality of openings and a plurality of edges. The laser-cut stent is then tumbled in a medium to round its edges and, in turn, to produce more rounded cross-sections of stent elements.

BRIEF DESCRIPTION OF THE DRAWINGS

The following drawings are illustrative of particular embodiments and therefore do not limit the scope of the invention, but are presented to assist in providing a proper understanding. The drawings are not to scale (unless so stated) and are intended for use in conjunction with the explanations of the following detailed description. The present invention will hereinafter be described in conjunction with the appended drawings, wherein like reference numerals denote like elements, and.

DETAILED DESCRIPTION OF THE EXEMPLARY EMBODIMENT

The following description is exemplary in nature and is not intended to limit the scope, applicability, or configuration of the invention in any way. Rather, the following description provides a convenient illustration for implementing an exemplary embodiment of the invention. Various changes to the described embodiment may be made in the function and arrangement of the elements described herein without departing from the scope of the invention.

Figure 1:
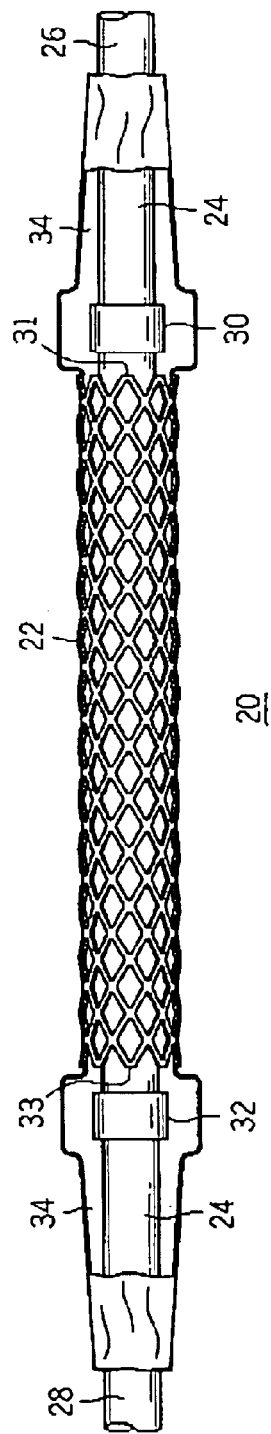
FIG. 1 is a longitudinal view, partially in cross-section, of a conventional balloon/stent assembly.

FIG. 1 is a longitudinal, cross-sectional view of a balloon/stent delivery system or assembly comprising an endovascular support device such as a laser-cut stent 22 having distal and proximal edges 31 and 33 respectively and an opening therethrough, an inner member or wire lumen 24 having a distal end 26 and a proximal end 28, and distal and proximal radiopaque marker bands 30 and 32 respectively which are positioned on inner member or wire lumen 24 near the distal and proximal ends of stent 22. It will be recognized by those skilled in the art that inner member or guide lumen 24 is configured for the insertion of a conventional guide wire (not shown) which will enable the balloon/stent assembly to be guided to and positioned at a target location in the vessel to be treated.

Any conventional or modified balloon catheter device may be used such as a PTCA balloon catheter. An expandable balloon portion 34 is mounted on inner member 24 in a compressed or collapsed state beneath stent 22 and extends beyond the proximal and distal ends of stent 22. Balloon 34 is generally made of a pliable material such as polyethylene, polyethylene terathalate, PEBAX (polyamide block copolymers and polyester block copolymers), polyvinyl chloride, polyolefin, nylon or the like. The length and the diameter of the balloon may be selected to accommodate the particular configuration of the stent to be deployed. Stent 22 may be constructed of any implantable material having good mechanical strength, such as implantable quality stainless steel. The outside or wall of stent 22 may be selectively plated with platinum or other implantable radiopaque substance to provide visibility during fluoroscopy. The cross-sectional shape of the tubular finished stent 22 may be circular, ellipsoidal, rectangular, hexagonal, square, or any other desired shape, although a circular or ellipsoidal cross-section is preferable. The length and width of stent 22 is generally determined to a large degree by the size of the vessel into which the stent will be deployed. Stent 22 must be of sufficient length to extend across a significant portion of the target area and maintain its axial orientation without shifting under the hydraulics of blood flow, while at the same time not be unnecessarily long so as to result in the introduction of a large amount of material into the vessel.

Stent 22 is compressed upon the outside of balloon 34. A temporary inner sheath (not shown) is placed over each end of balloon 34 and an exterior sheath (also not shown), is placed over the ends of the interior sheath so as to cover stent 22 and overlap with the interior sheaths. The assembly is then pressurized by introducing air or an inert gas such as nitrogen through the lumen 24 into the interior of balloon 34 thereby expanding the balloon within the sheaths. The assembly is then exposed to an elevated temperature while pressure in the balloon is maintained. The pressure may be, for example, approximately 70 psi and the temperature approximately 150 degrees Fahrenheit. Following heating, the balloon/stent assembly is allowed to cool within the sheaths, and this cooling sets the shape of balloon 34. The sheaths may then be removed. This process is described in detail in U.S. Pat. No. 5,836,965 entitled "Stent Delivery and Deployment Method" issued Nov. 17, 1998, the teachings of which are hereby incorporated by reference.

Marker bands 30 and 32, which may be viewed through fluoroscopy, assist in positioning the assembly. When the assembly is properly located across a lesion, the balloon may be inflated in a conventional manner. This results in the generally uniform, symmetrical expansion of the stent and balloon. The amount of inflation and thus the amount of expansion of the stent may be varied as dictated by the lesion itself.

Figure 2:
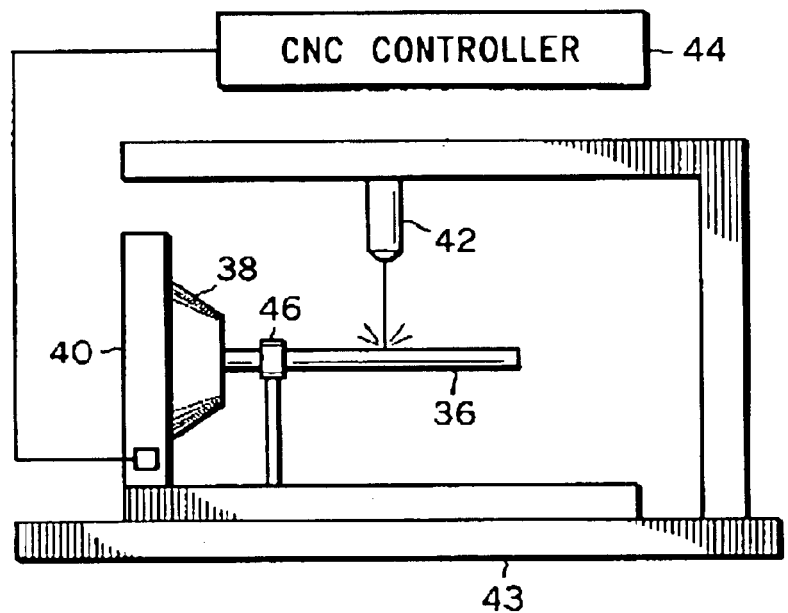
FIG. 2 is a schematic representation of an apparatus for selectively laser-cutting the tubing utilized in the manufacture a stent.

Referring to FIG. 2, there is shown a schematic representation of one example of an apparatus for selectively laser-cutting a tube in the manufacture of stent 22. A tube 36 of implantable metal is placed in a rotatable collet fixture 38 of a machine-controlled apparatus 40 such as a computer numerical control (CNC) that positions tube 36 relative to a laser 42. Laser 42 selectively removes material from the tube thereby cutting the tube into the discrete pattern of the finished stent. The process is fully automated except for the loading and unloading of the tube. This may be accomplished, for example, by using a CNC opposing collet fixture 38 which provides for axial rotation of tube 36 in conjunction with an X/Y table 43. X/Y table moves tube 36 axially relative to laser 42. The laser-cutting process may be controlled by means of a precision CNC controller 44, for example of the type manufactured and sold by Anorad Corporation. Alternatively, the discrete pattern may be produced by an etching process in accordance with well known etching techniques instead of laser-cutting.

Figure 4:
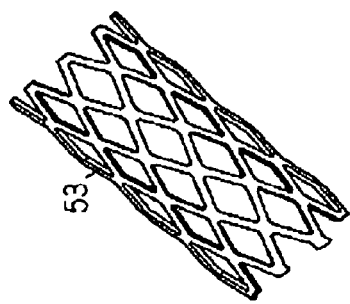
FIG. 4 is a longitudinal view of a stent in an expanded state after undergoing manufacture as described hereinbelow.
Figure 3:
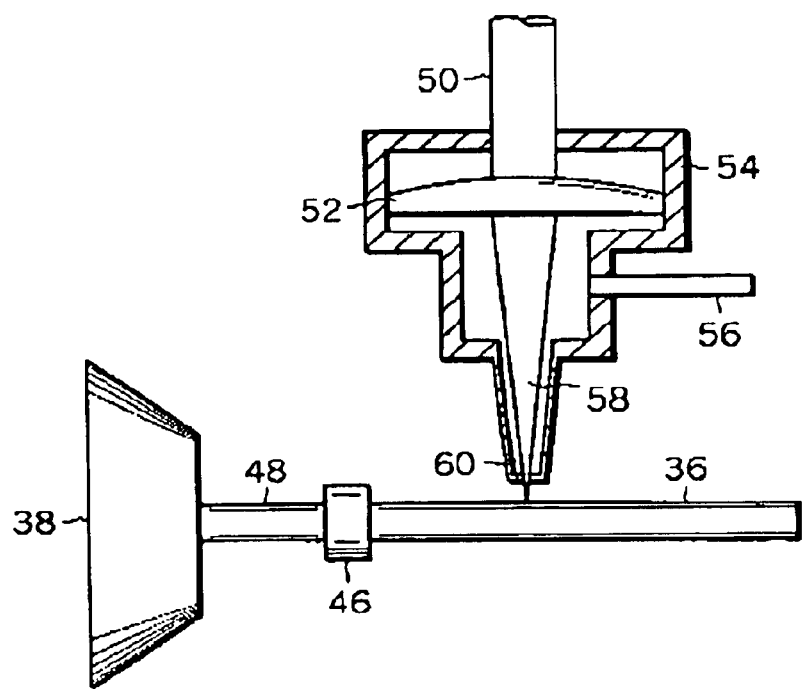
FIG. 3 is a more detailed view of the laser-cutting apparatus shown in FIG. 2.

FIG. 3 is a more detailed view of the laser-cutting apparatus shown in FIG. 2. As can be seen, tube 36 is supported by a CNC controlled rotary collet 38 and a bushing 46. Laser beam 50 is passed through a focusing lens 52 which is, in turn, surrounded by a coaxial gas jet assembly 54 having a gas input 56. In this manner, a gas stream that surrounds the focused laser beam 58 is directed along the laser beam axis to a coaxial gas jet nozzle 60. The gas jet (e.g. oxygen) reacts with the metal tube to assist in the cutting process. Focused laser beam 58 acts as an ignition source and controls the reaction of the oxygen with the metal in order to produce high-precision cuts in the metal. Mandrel 48 (e.g. made of stainless steel) is placed inside tube 36 and is free to roll on the bottom of the tube as the pattern is cut. A water-based cooling system (not shown) protects the inner far wall of tube 36 and acts as a beam/debris flush. After cutting, the stent may undergo several cleaning steps to remove loose debris. The result is a stent of the type shown in FIG. 4 in its expanded state. For a more detailed discussion of the above described direct laser-cutting process, the interested reader is directed to the above referenced patent.

Figure 6:
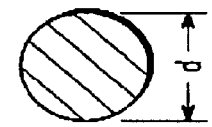
FIG. 6 is a cross-sectional view of the stent shown in FIG. 4 which has undergone further processing resulting in substantially smoother, rounded stent elements.
Figure 5:
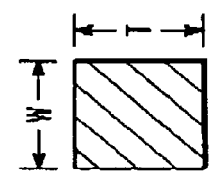
FIG. 5 is a cross-sectional view of one of the struts shown in FIG. 4.
Figure 7:
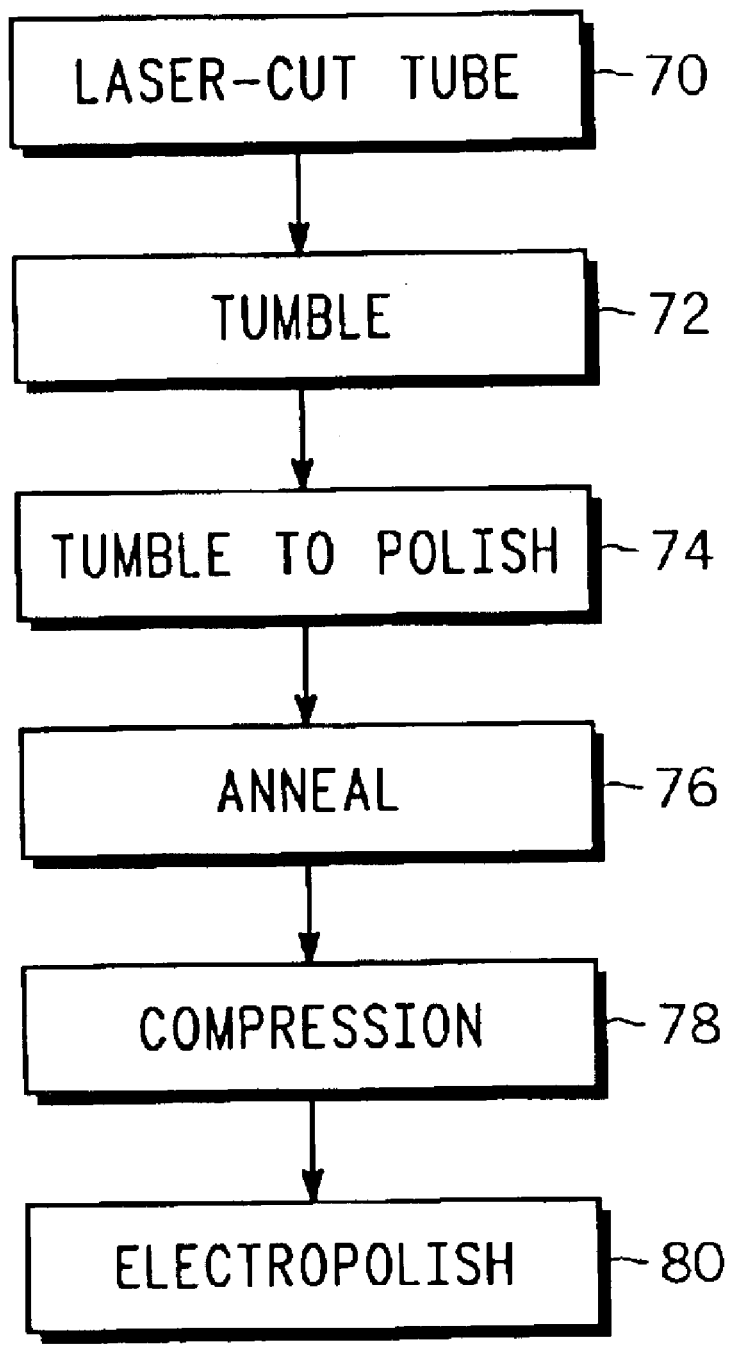
FIG. 7 is a flow-chart representing the manufacture of a laser-cut stent in accordance with the present invention.

As stated previously, direct laser-cutting of a stent from a tube results in the stent elements having a generally rectangular cross-section as is shown in FIG. 5. Thickness T may be approximately 0.004 inch to 0.010 inch and the width may be approximately 0.04 to 0.01 inch. The process thus far is represented by block 70 in FIG. 7 which represents the production of a laser-cut tube. For the reasons stated previously, the stent shown in FIG. 4 having the cross-section shown in FIG. 5 may be further processed to achieve a more rounded, substantially circular, cross-section of the type shown in FIG. 6. This may be accomplished by means of the inventive process illustrated in FIG. 7.

The laser-cut tube shown in FIG. 3 is tumbled in, for example, a water-based medium containing silica carbide powder and alumina impregnated with silica carbide for several hours (e.g. 2–6 hours) in a tumbling apparatus of the type available from Dreher Corporation of North Attleboro, Mass. and bearing model number 420 V/T. This is shown in block 72 of FIG. 7. If desired, the stent may be polished by tumbling the tube in, for example, a dry polishing media such as a crushed walnut-shell media as represented by block 74 of FIG. 7. The result is a stent having the desired dimensions, cross-section, and smoothness. The stent may then be annealed in a flash vacuum at approximately 1,100 degrees F. to create a homogenous crystalline microstructure as is shown at 76 in FIG. 7.

Since the stent was laser-cut in its expanded configuration, the stent may now be rolled down as, for example, between to parallel plates or compressed using a commercially available compression apparatus. This apparatus employs an iris which closes down circumferentially on the stent to compress it. This step of compression is represented by block 78 of FIG. 7. Finally, the compressed stent may undergo a simple electropolishing step for improving the corrosion resistance of the metal by attracting the chrome in the stainless steel to the surface of the stent as is represented by block 80 of FIG. 7.

Thus, there has been provided a method of manufacturing a laser-cut stent wherein the sharp edges of the rectangular cross-section created by the laser-cutting process are removed through a tumbling and polishing process. While a final electropolishing step may be employed, this is merely to provide corrosion resistance, and electropolishing is not depended upon to significantly alter the cross-section of the stent elements.

In the foregoing specification, the invention has been described with reference to a specific embodiment. However, it should be appreciated that various modifications and changes can be made without departing from the scope of the invention as set forth in the appended claims. Accordingly, the specification and figures should be regarded as illustrative rather than restrictive, and all such modifications are intended to be included within the scope of the present invention.

What is claimed is:

1. A method of manufacturing an endovascular support device, comprising:

positioning a generally tubular member of implantable metal having a generally cylindrical wall in a working relationship with a laser beam;

cutting a desired pattern in said generally cylindrical wall to produce a stein having a plurality of openings and a plurality of edges; and tumbling said stent in a water-based abrasive tumbling medium that contains silica carbide to round said plurality of edges.

2. A method of manufacturing an endovascular support device according to claim 1 wherein said generally tubular member is laser-cut in an expanded configuration and wherein said method further comprises radially compressing the laser-cut stent after said tumbling step.

3. A method of manufacturing an endovascular support device according to claim 2 further comprising electropolishing said laser-cut stent.

4. A method of manufacturing an endovascular support device according to claim 2 further comprising polishing said laser-cut stent prior to compressing.

5. A method of manufacturing an endovascular support device according to claim 4 wherein said implantable metal is stainless steel.

6. A method of manufacturing an endovascular support device according to claim 4 wherein said implantable metal is a cobalt-based alloy.

7. A method of manufacturing an endovascular support device according to claim 1 wherein the water-based abrasive medium further contains alumina impregnated with silica carbide.

8. A method of manufacturing an endovascular support device according to claim 7 wherein the step of tumbling further comprises a second step of tumbling said stent in a dry polishing medium.

9. A method of manufacturing an endovascular support device according to claim 8 wherein said dry polishing medium is a crushed walnut-shell medium.

10. A method of manufacturing an endovascular support device, comprising:

cutting a pattern in a wall of a tube of implantable metal to produce a stent having a plurality of openings and a plurality of edges;

tumbling said stent in a water-based abrasive tumbling medium that contains silica carbide to round said plurality of edges;

polishing said stent in a dry polishing medium;

radially compressing said stent; and electropolishing the compressed stent.

11. A method according to claim 10 wherein said cutting comprises laser cutting.

12. A method of manufacturing an endovascular support device according to claim 11 wherein said implantable metal is stainless steel.

13. A method of manufacturing an endovascular support device according to claim 11 wherein said implantable metal is a cobalt-based alloy.

14. A method of manufacturing an endovascular support device according to claim 10 wherein the water-based abrasive medium further contains alumina impregnated with silica carbide.

15. A method of manufacturing an endovascular support device according to claim 10 wherein said dry polishing medium is a crushed walnut-shell medium.

* * * * *